(12) United States Patent
Schroecker et al.

(10) Patent No.: US 9,747,709 B2
(45) Date of Patent: Aug. 29, 2017

(54) METHOD AND APPARATUS FOR ANIMATE VISUALIZATION OF STATIC 3-D DATA

(71) Applicant: General Electric Company, Schenectady, NY (US)

(72) Inventors: Gerald Schroecker, Salzburg (AT); Eduard Gröller, Vienna (AT); Alexey Karimov, Vienna (AT); Stefan Bruckner, Bergen (NO)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 77 days.

(21) Appl. No.: 14/576,369

(22) Filed: Dec. 19, 2014

(65) Prior Publication Data

US 2016/0174940 A1 Jun. 23, 2016

(51) Int. Cl.
| | |
|---|---|
| *G06T 15/08* | (2011.01) |
| *G06T 11/20* | (2006.01) |
| *A61B 8/00* | (2006.01) |
| *A61B 8/08* | (2006.01) |
| *G06T 13/80* | (2011.01) |
| *G06T 15/00* | (2011.01) |

(52) U.S. Cl.
CPC ............ *G06T 11/20* (2013.01); *A61B 8/0866* (2013.01); *A61B 8/4405* (2013.01); *A61B 8/461* (2013.01); *A61B 8/467* (2013.01); *G06T 13/80* (2013.01); *G06T 15/00* (2013.01); *G06T 15/08* (2013.01); *G06T 2207/10132* (2013.01); *G06T 2207/30044* (2013.01)

(58) Field of Classification Search
None
See application file for complete search history.

(56) References Cited

U.S. PATENT DOCUMENTS

| | | | |
|---|---|---|---|
| 6,019,723 A | 2/2000 | Yamaura | |
| 2006/0270938 A1 | 11/2006 | Yawata | |
| 2008/0117209 A1* | 5/2008 | Razeto | G06T 7/0081 345/424 |
| 2011/0170752 A1* | 7/2011 | Martin | G09B 23/285 382/128 |
| 2011/0301451 A1* | 12/2011 | Rohling | A61B 8/00 600/424 |

OTHER PUBLICATIONS

Malcom Kesson, "Using Noise," https://web.archive.org/web/20100628034727/http://www.fundza.com/rman_shaders/noino/index.html, Jun. 2010.*
Voxelogic, "Acropora," https://web.archive.org/web/20101003075448/http://www.voxelogic.com/index.php?optiop=com_content&view=article&id=1&Itemid=21, 2010.*
Chris Zwar, "Fractal Noise a New Look at an Old Friend," https://library.creativecow.net/articles/zwar_chris/fractal_noise.php, 2006.*

(Continued)

*Primary Examiner* — Nicholas R Wilson
(74) *Attorney, Agent, or Firm* — Grogan, Tuccillo & Vanderleeden, LLP

(57) ABSTRACT

Rendering a time sequence of 2-D images includes obtaining ultrasound image data, applying time variant noise, and raytracing the ultrasound image data to render pixels of a 2-D image for each of a plurality of time steps.

22 Claims, 4 Drawing Sheets

(56) References Cited

OTHER PUBLICATIONS

Ahmed Fathy Mosaad Elnokrashy; "New Methodologies for Processing Medical Images"; Thesis; 2014; pp. iii-76; Giza, Egypt.
Unity Resourses; Script: Perlin Noise; webpage: http://www.auto.tuwien.ac.at/wordpress/?tag=perlin. 2011.
Unify Community Wiki; Perlin Noise; webpage: http://wiki.unity3d.com/index.php/Perlin_Noise. 2013.
Perlin Noise in Animation; webpage: http://research.cs.wisc.edu/graphics/Courses/cs-838-1999/Students/fruit/final_writeup.html, 1999.
Unity Answers; "How to Randomly Change the Intensity of a Point Light with a Script"; webpage: http://answers.unity3d.com/questions41931/how-to-randomly-change-the-intensity-of-a-point-li.html, 2011.
Arvid Nilsson; Karl-Johan Arklid; "Project Candle Flame in EDAN35 High Performance Computer Graphics"; pp. 1-2; Lund University; Sweden. 2012.

* cited by examiner

```
For every (x , y) pixel in the output image
        float4 f4Color=0 ;
        for every depth step z in depth
                float3 f3Offset = gradient (noise _4D
(t, x, y, z)); // special kind of flow noise
                float intensity = inputVolume ((x, y, z)
+f3Offset) + noise_4D (t, x, y, z) ;
                float4 f4Sample = transfer (intensity, t, x, y) ;
                // rgb=color, a=alpha
                float3 f3Gradient = gradient (inputVolume
(x, y, z)) ;   // computed with e.g. central
differences, points in direction of strongest change
                float fBrightness = f3LightColor * max (0 , dot
(normalize (f3Gradient) , f3LightDirection)) ; // very
simple diffuse shading
                f4Ccolor += (1 - f4Color.a) *
                f4Sample*f3Brightness;
        end
    end
```

METHOD AND APPARATUS FOR ANIMATE VISUALIZATION OF STATIC 3-D DATA

BACKGROUND

Technical Field

Embodiments of the invention relate generally to ultrasound medical imaging. Particular embodiments relate to fetal ultrasound imaging.

Discussion of Art

Generally, ultrasound medical imaging is used to survey internal structures for diagnostic purposes. Ultrasound imaging has comparatively short acquisition times per image (on the order of one tenth of a second as compared to several seconds for MRI), can acquire many images with minimal patient risk, and offers a unique role for an ultrasound technician as part of the imaging system control loop. It therefore is particularly used for imaging moving internal structures, e.g., for fetal imaging during gestation.

With reference to fetal imaging, ultrasound imaging serves more than merely diagnostic purposes. The presentation of a live image to prospective parents can promote emotional bonding of the parents to their prospective offspring, thereby enhancing motivation to comply with well-baby practices recommended by the obstetric professional involved in the case.

The emotional engagement of a live fetal image can, however, be distracting from important counseling materials that obstetric professionals seek to present. Additionally, although ultrasound fetal imaging is a relatively comfortable and low-risk procedure, certain aspects of the imaging procedure are themselves distracting and detract from attention to counseling materials.

In view of the above, it is desirable to provide apparatus and methods for approximating a live fetal image, outside of the ultrasound imaging setting, and with less distraction than typically arises from a fully live fetal image.

BRIEF DESCRIPTION

Embodiments of the invention implement a method, which includes obtaining ultrasound image data and rendering a time sequence of 2-D images from the ultrasound image data. Rendering the time sequence of 2-D images includes applying time variant noise and raytracing the ultrasound image data to render pixels of a 2-D image for each of a plurality of time steps.

Other embodiments provide an ultrasound diagnostic apparatus, which includes an ultrasonic probe; a generating unit operatively connected with the ultrasonic probe and configured to obtain ultrasound image data from the ultrasonic probe; and a display processing unit operatively connected with the generating unit and configured to render a time sequence of 2-D images from the ultrasound image data.

Yet other embodiments provide non-transitory computer readable media, which is encoded with a time sequence of 2-D images obtained from ultrasound image data by applying time variant noise to voxels of the ultrasound image data for each of a plurality of time steps, and raytracing the ultrasound image data to render pixels of a 2-D image for that time step.

DRAWINGS

The present invention will be better understood from reading the following description of non-limiting embodiments, with reference to the attached drawings, wherein below:

FIG. 3 shows pseudocode for raytracing voxels to provide a 2-D image according to an embodiment of the invention.

DETAILED DESCRIPTION

Figure 1:
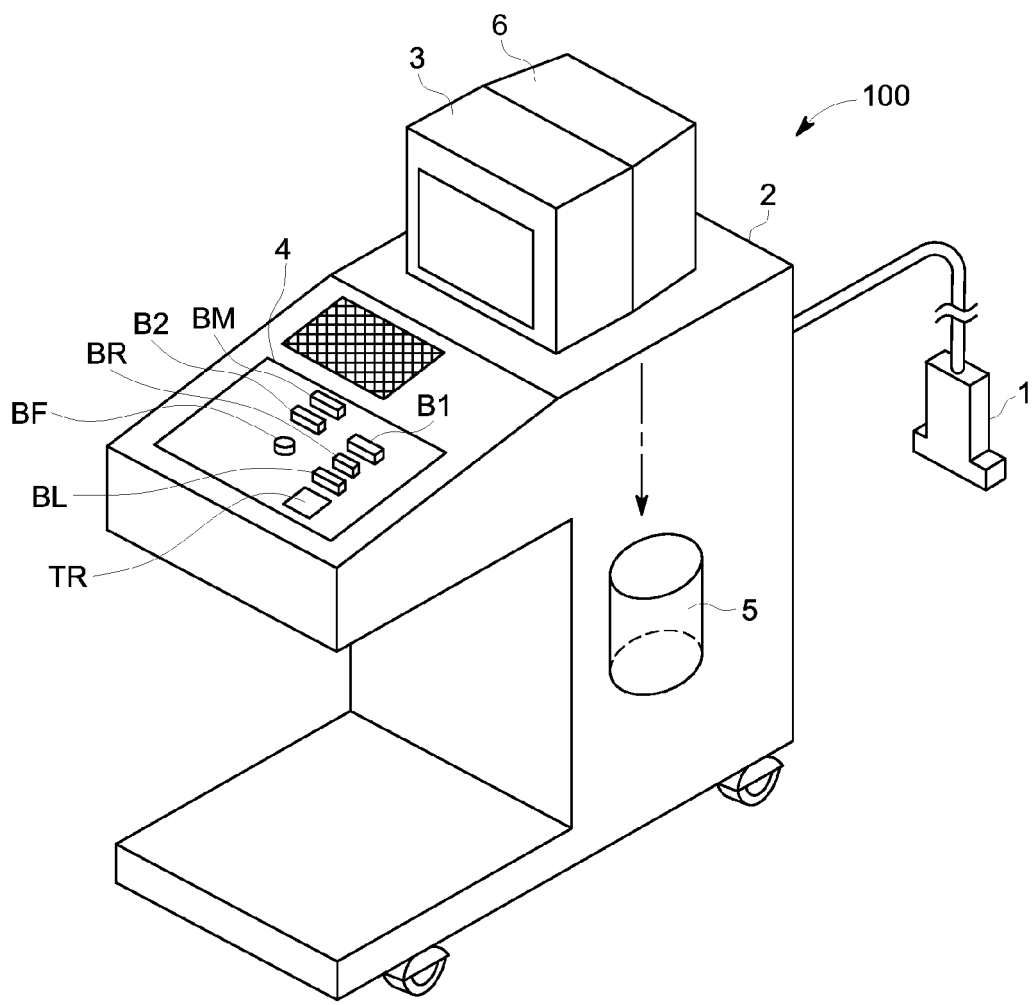
FIG. 1 is a perspective view schematically showing an ultrasound diagnostic apparatus in a mode for implementing an embodiment of the present invention.

Reference will be made below in detail to exemplary embodiments of the invention, examples of which are illustrated in the accompanying drawings. Wherever possible, the same reference characters used throughout the drawings refer to the same or like parts, without duplicative description. Although exemplary embodiments of the present invention are described with respect to fetal imaging, embodiments of the invention also are applicable for use in approximating live ultrasound images, generally.

As used herein, the terms "substantially," "generally," and "about" indicate conditions within reasonably achievable manufacturing and assembly tolerances, relative to ideal desired conditions suitable for achieving the functional purpose of a component or assembly.

By way of background, embodiments of the present invention may be utilized with ultrasound diagnostic apparatus such as the apparatus 100 depicted in FIG. 1. As shown, the apparatus 100 includes an ultrasonic probe 1 which transmits an ultrasonic pulse into a subject, e.g., the body of a human patient, and receives an ultrasonic echo from within the subject. The apparatus 100 further includes an ultrasound diagnostic apparatus body 2, which generates an ultrasound image on the basis of the ultrasonic echo, and a monitor 3 that displays the ultrasound image. The ultrasound diagnostic apparatus body 2 is provided with an operation panel 4, which accepts the operator's instructions, and a storage device 5 for storing ultrasound images and values of each item measured from the ultrasound images. The operation panel 4 includes conventional ultrasound imaging controls including, for example, an image list button BM, a record button B1, an image pickup condition recall button B2, a display zoom button BR, a freeze button BF, a position record button BL, and a cursor track ball TR. The storage device 5 is, for example, a hard drive.

The apparatus 100 further includes a display processing unit 6. An example of actual hardware of the display processing unit 6 may conceivably comprise a CPU (central processing unit) which performs processing, a ROM (read only memory) in which a program of the above-described configuration is stored dedicated to reading, and a RAM (random access memory) which can be used as a working area and rewritably stores various data, all connected by a bus.

In the ultrasound diagnostic apparatus 100, the ultrasonic probe 1 emits one or more ultrasonic pulses scheduled at a pulse repetition frequency ("PRF") and recovers ultrasonic echo signals that are returned from the subject to a plurality of two-dimensionally distributed sampling points. The ultrasonic probe 1 transduces the ultrasonic echo signals into digital data that is sent to the display processing unit 6. The display processing unit 6 then generates ultrasound images on the basis of the digital data provided from the ultrasonic probe 1, and sends the ultrasound images to the monitor or other display 3.

Embodiments of the present invention address an aesthetic deficiency of conventional ultrasound systems similar to the ultrasound diagnostic apparatus 100. The aesthetic deficiency of conventional systems is that the freeze button BF conventionally has caused the image display processing unit 6 to output image signals of a completely still ultrasound image. Although for purely diagnostic purposes a still image is desirable, ultrasound images also are used for patient counseling and for wellness promotion. In such uses, especially for pre-natal or fetal ultrasound imaging, it can be desirable to establish an emotional engagement of the patient with their ultrasound image. Still ultrasound images convey an aesthetic of clinical detachment and objectivism. On the other hand, it is neither feasible nor even desirable to provide a live-action ultrasound image within a setting otherwise conducive to thoughtful discussion. The apparatus and patient posture required for live ultrasound is not comfortable, and many patients find it awkward to discuss medical options or well-baby checkup schedules while slathered with gel. Moreover, live video of one's own fetus often is far more engaging than most things that a medical professional can have to say. Therefore, it is desirable to provide a compromise ultrasound image that is neither live-action nor still, and that promotes some emotional engagement of a patient with the image without making the image the sole focus of the patient's attention.

Figure 2:
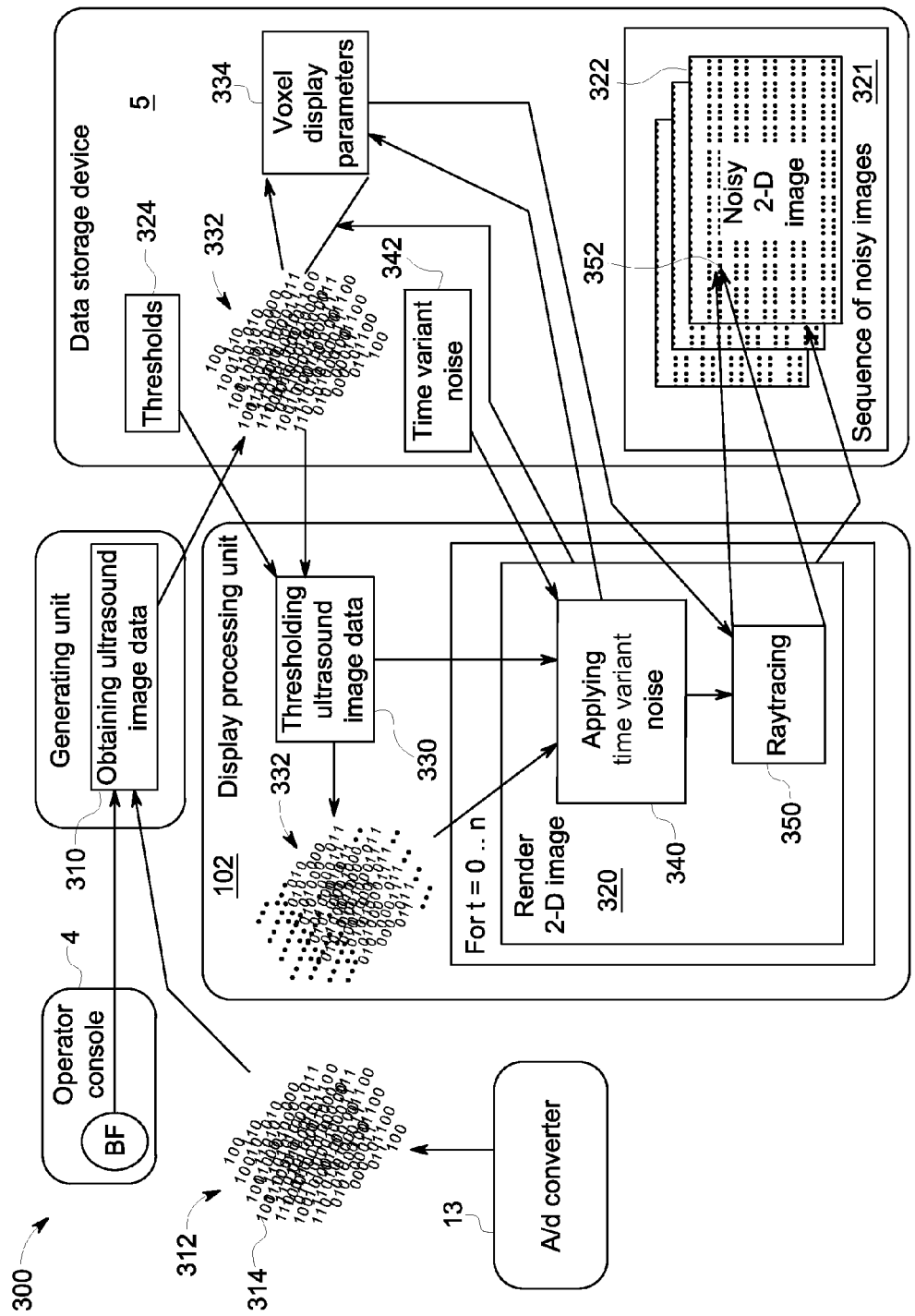
FIG. 2 is a schematic showing a method for approximating a live fetal image, according to an embodiment of the invention.

FIG. 2 illustrates a method 300 for approximating a live fetal image, according to aspects of the invention. Exemplary embodiments of the method 300 include obtaining 310 a set of ultrasound image data 312 (which includes, essentially, a 3-D matrix of intensity values 314); and then rendering 320 a time sequence 321 of noisy 2-D images 322 from the ultrasound image data 312. The process of rendering 320 includes each time step applying 340 time variant noise 342 (i.e., noise that changes as a function of time) to at least one parameter 334 (e.g., color and/or opacity) of some or all of the ultrasound image data 312. For example, certain implementations may include first thresholding 330 the ultrasound image data 312 (e.g., based on comparison of an ultrasound image scalar 314, such as an intensity value, against a flat threshold 324) in order to identify low-information voxels 332 (i.e., voxels 314 that have a parameter, such as intensity, that is less than a pre-determined threshold value), then rendering 320 display parameters 334 for each of the voxels of the ultrasound image data 312, then applying the noise 342 to at least one display parameter 334 of each of the low-information voxels 332. The rendering process 320 further includes raytracing 350 from each display pixel 352 through underlying voxels of the ultrasound image data 312 (including voxels 332 to which the time variant noise 342 has been applied 340) in order to generate one of the noisy 2-D images 322. The voxel raytracing 350 can be accomplished, for example, according to pseudocode as shown in FIG. 3.

Therefore, in each of the noisy 2-D images 322 the display parameter(s) 334 of a given low-information voxel 332 most likely will have different value(s) from those of the same low-information voxel 332 in any other of the noisy 2-D images 322. By contrast, the display parameters 334 of all other voxels in the ultrasound image data 312 (those voxels that are not low-information voxels 332) will be constant across all of the noisy 2-D images 322.

The sequence 321 of noisy 2-D images 322 then can be displayed, e.g., to a patient during a medical presentation or counseling session. The significant voxels will be steady in appearance, whereas the low-information voxels 332 will vary in appearance in such a way as to enliven the image sequence 321.

The time variant noise 342 can be 1-D (e.g., one or more of the display parameter(s) 334 are identically adjusted for all of the low-information voxels 332 at any given moment of time), 2-D (e.g., the display parameter 334 is identically adjusted, at any given moment of time, only for all of the low-information voxels 332 that are on a common plane within the matrix of ultrasound image data 312; or, for all of the low-information voxels 332, two display parameters 334 are differently adjusted at any given moment), 3-D (e.g., the display parameter 334 is identically adjusted, at any given moment of time, only for all of the low-information voxels 332 that are on a common line within the matrix of ultrasound image data 312; or, for all of the low-information voxels 332 that are on a common plane within the matrix of ultrasound image data 312, two display parameters 334 are differently adjusted at any given moment; or, for all of the low-information voxels 332, three display parameters 334 are differently adjusted at any given moment), or 4-D (e.g., one or more display parameter(s) 334 may be adjusted differently, at any given moment of time, for each of the low-information voxels 332 within the matrix of ultrasound image data 312).

The time variant noise 342 can be applied to one or more display parameters 334 of individual low-information voxels 332, e.g., color components, opacity. The time variant noise 342, also, or alternatively, can be applied to one or more render parameters 346 (e.g., lighting color, direction, or position; camera position, orientation, or focus) that will affect all pixels of the noisy 2-D image 322; or to render parameters 346 that may "naturally" vary per pixel of the 2-D image, i.e., render parameters that relate to a participating medium, such as refractive index or transfer functions for clarity or color.

Thus, multi-dimensional time variant noise 342 can be multi-dimensional across space (e.g., differing noise values at a same moment of time, according to x,y,z coordinates of each low-information voxel 332) and/or across display parameter(s) 334 (e.g., differing noise values for different display parameters at a same moment of time, for some or all of the low-information voxels 332).

Figure 4A:
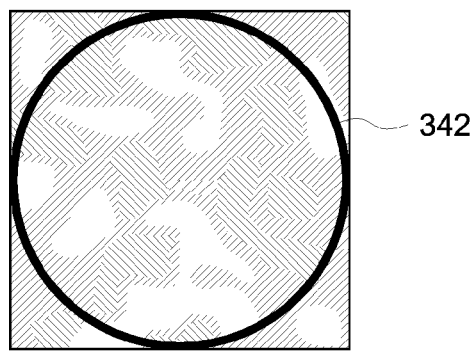
FIGS. 4A-4B are images illustrating how to generate a cyclic noise waveform used in embodiments of the invention.
Figure 4B:
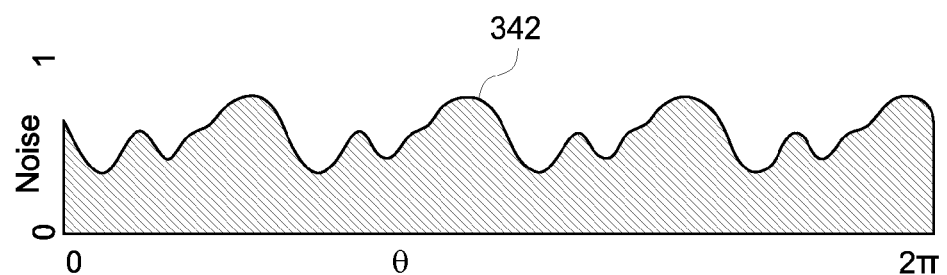

Generally, time variant noise 342 can be produced from one or more random waveforms, obtained for example as shown in FIGS. 4A-4B ("Perlin" noise). Simplex noise also can be used. Cyclic random waveforms, as shown in FIGS. 4A-4B can be utilized so as to enable the time variant noise to play continuously from a relatively small stored image size. For 1-D noise only one cyclic random waveform is needed (along the axis of time), whereas for multi-dimensional noise, a vector sum of several orthogonal waveforms can be used. In some embodiments (e.g., in which the noise is accumulatively added to a display parameter, e.g., brightness) it may be desirable to use a derivative of the random cyclic waveform, e.g., its slope, so as to avoid continually incrementing the display parameter to, e.g., an unbearable brightness.

According to some embodiments of the invention, the method 300 can be implemented in the display processing unit 6. For example, the method 300 can be implemented entirely in response to a press of the freeze button BF at the operator console 4. The display processing unit 6 then can save the sequence 321 of noisy 2-D images 322 to the storage device 5, for later retrieval. For example, the noisy 2-D images 322 can be rendered 320 during a normal fetal ultrasound procedure, then later displayed in order to enhance patient emotional engagement in counseling while in a setting that is conducive to patient attentiveness.

Advantageously, configuration of the ultrasound diagnostic apparatus 100 to provide the time sequence 321 of noisy 2-D images 322 enables novel uses of the ultrasound diagnostic apparatus 100 to improve patient outcomes by, for example, synergistically improving patient attention to medical counseling and patient engagement/emotional investment in adhering to counseling.

Thus, embodiments of the invention implement a method, which includes obtaining ultrasound image data and rendering a time sequence of 2-D images from the ultrasound image data. Rendering the time sequence of 2-D images includes applying time variant noise, and raytracing the ultrasound image data to render pixels of a 2-D image for each of a plurality of time steps. For example, the ultrasound image data may include low-information voxels at which a value of at least one render parameter may be less than a pre-determined threshold. The time variant noise may be applied to at least one parameter of each low-information voxel, and/or to at least one display parameter of each voxel of the ultrasound image data. The time variant noise may be applied to at least one render parameter of the 2-D image. For example, render parameters may include one or more of: light intensity, position, orientation, or color; camera position, orientation, or focus; participating media refractive index or transfer functions for clarity or color; or opacity or color of the static 3-D model. The time variant noise may be 1-D, or may be multi-dimensional. In some embodiments, the method may also include displaying the noisy 2-D image. In some embodiments, the time variant noise may be cyclic. The time variant noise may be applied to spatially displace the ultrasound image data.

Other embodiments of the invention provide an ultrasound diagnostic apparatus, which includes an ultrasonic probe, a generating unit operatively connected with the ultrasonic probe and configured to obtain ultrasound image data from the ultrasonic probe, and a display processing unit that is operatively connected with the generating unit and configured to render a time sequence of 2-D images from the ultrasound image data. For example, the display processing unit may be configured to render the time sequence of 2-D images by applying time variant noise to voxels of the ultrasound image data over a sequence of time steps and rendering a 2-D image for each of the time steps. The display processing unit may be configured to apply the time variant noise to at least one display parameter of the voxels, and/or to apply the time variant noise to at least one render parameter of the 2-D image.

Yet other embodiments provide non-transitory computer readable media, which is encoded with a time sequence of 2-D images obtained from ultrasound image data by applying time variant noise to voxels of the ultrasound image data for each of a plurality of time steps, and raytracing the ultrasound image data to render pixels of a 2-D image for each time step. The time variant noise may be applied to at least one render parameter of the 2-D image, and the at least one render parameter may include one or more of: light intensity, position, orientation, or color; camera position, orientation, or focus; participating media refractive index or transfer functions for clarity or color.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, terms such as "first," "second," "third," "upper," "lower," "bottom," "top," etc. are used merely as labels, and are not intended to impose numerical or positional requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose several embodiments of the invention, including the best mode, and also to enable one of ordinary skill in the art to practice embodiments of the invention, including making and using any devices or systems and performing any incorporated methods. The patentable scope of the invention is defined by the claims, and may include other examples that occur to one of ordinary skill in the art. Such other examples are intended to be within the scope of the claims if they have structural elements that do not differ from the literal language of the claims, or if they include equivalent structural elements with insubstantial differences from the literal language of the claims.

As used herein, an element or step recited in the singular and proceeded with the word "a" or "an" should be understood as not excluding plural of the elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

Since certain changes may be made in the above-described method, apparatus, and media, without departing from the spirit and scope of the invention herein involved, it is intended that all of the subject matter of the above description or shown in the accompanying drawings shall be interpreted merely as examples illustrating the inventive concept herein and shall not be construed as limiting the invention.

What is claimed is:

1. An ultrasound diagnostic apparatus comprising:
   an ultrasonic probe;
   a generating unit operatively connected with the ultrasonic probe and configured to obtain ultrasound image data from the ultrasonic probe; and
   a display processing unit operatively connected with the generating unit; and
   wherein the display processing unit is configured to render a time sequence of 2-D images from the ultrasound image data by:

identifying low-information voxels in the ultrasound image data;
applying time variant noise to at least one display parameter of each of the identified low-information voxels to simulate movement; and
raytracing the ultrasound image data for each of a plurality of time steps.

2. The apparatus of claim 1, wherein the display processing unit is configured to apply the time variant noise to at least one render parameter of at least one of the 2-D images.

3. The apparatus of claim 2, wherein the at least one render parameter includes one or more of: light intensity, position, orientation, or color; camera position, orientation, or focus; participating media refractive index or transfer functions for clarity or color.

4. The apparatus of claim 1, wherein the time variant noise is 1-D.

5. The apparatus of claim 1, wherein the time variant noise is multi-dimensional.

6. The apparatus of claim 1, further configured to display the 2-D images.

7. The apparatus of claim 1, wherein the time variant noise is cyclic.

8. The apparatus of claim 1, wherein the time variant noise is applied to spatially displace the ultrasound image data.

9. A non-transitory computer readable medium storing instructions executed by a display processing unit of an ultrasound diagnostic apparatus to:
identify low-information voxels in obtained ultrasound image data, wherein one or more ultrasound images are generated from the ultrasound image data;
apply time variant noise to at least one display parameter of each of the identified low-information voxels to simulate movement; and
raytrace the ultrasound image data to render pixels of a 2-D image for each of a plurality of time steps.

10. The non-transitory computer readable medium of claim 9, wherein the time variant noise is applied to at least one render parameter of the 2-D image, wherein the at least one render parameter includes one or more of: light intensity, position, orientation, or color; camera position, orientation, or focus; participating media refractive index or transfer functions for clarity or color.

11. The non-transitory computer readable medium of claim 9, wherein the time variant noise is 1-D.

12. The non-transitory computer readable medium of claim 9, wherein the time variant noise is multi-dimensional.

13. The non-transitory computer readable medium of claim 9, wherein the time variant noise is cyclic.

14. A method for rendering a time sequence of 2-D ultrasound images comprising:
identifying low-information voxels in obtained ultrasound image data, wherein one or more ultrasound images are generated from the ultrasound image data;
applying time variant noise to at least one display parameter of each of the identified low-information voxels to simulate movement; and
raytracing the ultrasound image data to render pixels of a 2-D image for each of a plurality of time steps.

15. The method of claim 14, wherein the low-information voxels are those at which a value of at least one render parameter is less than a pre-determined threshold.

16. The method of claim 14, wherein the time variant noise is applied to at least one render parameter of the 2-D image.

17. The method of claim 16, wherein the at least one render parameter includes one or more of: light intensity, position, orientation, or color; camera position, orientation, or focus; participating media refractive index or transfer functions for clarity or color.

18. The method of claim 14, a wherein the time variant noise is 1-D.

19. The method of claim 14, a wherein the time variant noise is multi-dimensional.

20. The method of claim 14, further comprising displaying the 2-D image.

21. The method of claim 14, a wherein the time variant noise is cyclic.

22. The method of claim 14, a wherein the time variant noise is applied to spatially displace the ultrasound image data.

* * * * *